(12) United States Patent
Hanson et al.

(10) Patent No.: US 11,135,356 B2
(45) Date of Patent: Oct. 5, 2021

(54) CONTROLLED DELIVERY DRIVE MECHANISMS FOR DRUG DELIVERY PUMPS

(71) Applicant: UNL Holdings LLC, New York, NY (US)

(72) Inventors: Ian B. Hanson, Wayne, PA (US); Scott Beaver, San Marcos, CA (US); Paul F. Bente, IV, Wayne, PA (US); Kevin Bokelman, San Diego, CA (US); Mark Majette, San Diego, CA (US)

(73) Assignee: UNL Holdings LLC, New York, NY (US)

( * ) Notice: Subject to any disclaimer, the term of this patent is extended or adjusted under 35 U.S.C. 154(b) by 132 days.

(21) Appl. No.: 15/967,208

(22) Filed: Apr. 30, 2018

(65) Prior Publication Data

US 2018/0243502 A1 Aug. 30, 2018

Related U.S. Application Data

(62) Division of application No. 14/423,599, filed as application No. PCT/US2013/057367 on Aug. 29, 2013, now Pat. No. 10,092,693.

(Continued)

(51) Int. Cl.
*A61M 5/145* (2006.01)
*A61M 5/168* (2006.01)
*A61M 5/142* (2006.01)

(52) U.S. Cl.
CPC ........ *A61M 5/1454* (2013.01); *A61M 5/1452* (2013.01); *A61M 5/14546* (2013.01);

(Continued)

(58) Field of Classification Search
CPC ........... A61M 2005/14208; A61M 2202/0007; A61M 2205/3334; A61M 5/1452;

(Continued)

(56) References Cited

U.S. PATENT DOCUMENTS 3,631,847 A   1/1972  Hobbs, II
3,701,345 A   10/1972 Heilman
(Continued)

FOREIGN PATENT DOCUMENTS

EP   1702635 A2   9/2006
EP   1341569 B1   1/2007
(Continued)

OTHER PUBLICATIONS

International Search Report and Written Opinion from PCT/US2013/057367, entitiled, "Controlled Delivery Drive Mechanisms for Drug Delivery Pumps," (May 27, 2014) 11 pages.

(Continued)

*Primary Examiner* — Quynh-Nhu H. Vu
(74) *Attorney, Agent, or Firm* — Hamilton, Brook, Smith & Reynolds, P.C.

(57) ABSTRACT

A controlled delivery drive mechanism includes a drug container having a barrel and a plunger seal; a drive housing within which at least initially partially resides a piston having an interface surface and a drive rack; and a power spring. The piston is configured to contact and axially translate the plunger seal within barrel. The mechanism may be configured to convert rotational movement of a drive pinion to axial translation of the drive rack, or to convert axial force of a linear power spring into torsional motion of a drive pinion. A regulating mechanism meters the drive pinion such that the piston is axially translated at a controlled rate. The drug container may contain a drug fluid within a drug chamber for drug delivery at a controlled rate.

(Continued)

The regulating mechanism may be an escapement regulating mechanism. A drug delivery pump includes such controlled delivery drive mechanisms.

8 Claims, 9 Drawing Sheets

Related U.S. Application Data

(60) Provisional application No. 61/694,534, filed on Aug. 29, 2012, provisional application No. 61/731,744, filed on Nov. 30, 2012, provisional application No. 61/748,667, filed on Jan. 3, 2013.

(52) U.S. Cl.
CPC .... *A61M 5/14566* (2013.01); *A61M 5/16804* (2013.01); *A61M 2005/14208* (2013.01); *A61M 2202/0007* (2013.01); *A61M 2205/3334* (2013.01)

(58) Field of Classification Search
CPC ............ A61M 5/1454; A61M 5/14546; A61M 5/14566; A61M 5/16804; A61M 5/142; A61M 5/145; A61M 2005/14506; A61M 2005/3152; A61M 5/31558; A61M 5/31575; A61M 5/20; A61M 5/315
See application file for complete search history.

(56) References Cited

U.S. PATENT DOCUMENTS

| | | | |
|---|---|---|---|
| 3,886,938 A * | 6/1975 | Szabo | A61M 5/1454 604/135 |
| 4,004,586 A | 1/1977 | Christensen et al. | |
| 4,313,439 A | 2/1982 | Babb et al. | |
| 4,565,543 A | 1/1986 | Bekkering et al. | |
| 4,602,700 A | 7/1986 | Szabo | |
| 4,668,220 A * | 5/1987 | Hawrylenko | A61M 5/1454 128/DIG. 1 |
| 4,673,400 A | 6/1987 | Martin | |
| 4,676,122 A | 6/1987 | Szabo et al. | |
| 4,685,903 A | 8/1987 | Cable et al. | |
| 4,755,172 A * | 7/1988 | Baldwin | A61M 5/1454 604/131 |
| 4,755,173 A | 7/1988 | Konopka et al. | |
| 4,840,620 A | 6/1989 | Kobayashi et al. | |
| 4,921,487 A | 5/1990 | Buffet et al. | |
| 5,167,816 A | 12/1992 | Kruger et al. | |
| 5,747,350 A | 5/1998 | Sattler | |
| 5,795,339 A | 8/1998 | Erskine | |
| 5,858,001 A | 1/1999 | Tsals et al. | |
| 5,919,167 A | 7/1999 | Mulhauser et al. | |
| 6,248,093 B1 | 6/2001 | Moberg | |
| 6,645,177 B1 | 11/2003 | Shearn | |
| 6,699,218 B2 | 3/2004 | Flaherty et al. | |
| 6,802,394 B2 * | 10/2004 | Patterson | F16N 11/04 184/105.1 |
| 7,063,684 B2 | 6/2006 | Moberg | |
| D564,087 S | 3/2008 | Yodfat et al. | |
| D585,543 S | 1/2009 | Yodfat et al. | |
| 7,479,135 B2 | 1/2009 | Richter et al. | |
| 7,611,503 B2 | 11/2009 | Spohn et al. | |
| 7,780,636 B2 | 8/2010 | Radmer et al. | |
| 7,803,134 B2 | 9/2010 | Sharifi et al. | |
| 7,846,132 B2 | 12/2010 | Gravesen et al. | |
| 7,879,010 B2 | 2/2011 | Nunn et al. | |
| 7,905,859 B2 | 3/2011 | Bynum et al. | |
| 7,927,306 B2 | 4/2011 | Cross et al. | |
| 7,967,795 B1 | 6/2011 | Cabiri | |
| 8,029,472 B2 | 10/2011 | Leinsing et al. | |
| 8,048,031 B2 | 11/2011 | Shaw et al. | |
| 8,152,771 B2 | 4/2012 | Mogensen et al. | |
| 8,157,769 B2 | 4/2012 | Cabiri | |
| 8,162,892 B2 | 4/2012 | Mogensen et al. | |
| 8,167,844 B2 | 5/2012 | Dillard, III | |
| 8,187,232 B2 | 5/2012 | Chong et al. | |
| D669,165 S | 10/2012 | Estes et al. | |
| 8,795,234 B2 | 8/2014 | Kadamus et al. | |
| 8,939,935 B2 | 1/2015 | O'Connor et al. | |
| 9,005,169 B2 | 4/2015 | Gravesen et al. | |
| 9,987,419 B2 | 6/2018 | Hanson et al. | |
| 10,092,693 B2 | 10/2018 | Hanson et al. | |
| 10,695,487 B2 | 6/2020 | Hanson et al. | |
| 2002/0123740 A1 | 9/2002 | Flaherty et al. | |
| 2004/0039344 A1 | 2/2004 | Baldwin et al. | |
| 2004/0092878 A1 | 5/2004 | Flaherty | |
| 2005/0171476 A1 | 8/2005 | Judson | |
| 2005/0197625 A1 | 9/2005 | Haueter et al. | |
| 2006/0069355 A1 * | 3/2006 | Judson | A61M 5/31511 604/211 |
| 2007/0010789 A1 | 1/2007 | Peter et al. | |
| 2007/0059989 A1 | 3/2007 | Kura et al. | |
| 2007/0073228 A1 | 3/2007 | Mernoe et al. | |
| 2007/0173762 A1 | 7/2007 | Estes et al. | |
| 2007/0179444 A1 | 8/2007 | Causey et al. | |
| 2008/0132842 A1 | 6/2008 | Flaherty | |
| 2008/0269687 A1 | 10/2008 | Chong et al. | |
| 2009/0093792 A1 | 4/2009 | Gross et al. | |
| 2009/0124979 A1 | 5/2009 | Raymond et al. | |
| 2009/0145509 A1 | 6/2009 | Baker et al. | |
| 2009/0204077 A1 | 8/2009 | Hasted et al. | |
| 2009/0240240 A1 | 9/2009 | Hines et al. | |
| 2011/0098652 A1 | 4/2011 | Hasted et al. | |
| 2011/0160650 A1 | 6/2011 | Chong et al. | |
| 2011/0166509 A1 | 7/2011 | Gross et al. | |
| 2011/0301534 A1 | 12/2011 | Renz et al. | |
| 2012/0035546 A1 | 2/2012 | Cabiri | |
| 2012/0078184 A1 | 3/2012 | Smith | |
| 2012/0123354 A1 | 5/2012 | Woehr | |
| 2012/0172804 A1 | 7/2012 | Plumptre | |
| 2012/0172815 A1 * | 7/2012 | Holmqvist | A61M 5/31578 604/208 |
| 2013/0046276 A1 * | 2/2013 | Mernoe | A61M 5/14566 604/500 |
| 2013/0060196 A1 | 3/2013 | O'Connor et al. | |
| 2013/0060233 A1 | 3/2013 | O'Connor et al. | |
| 2014/0200510 A1 | 7/2014 | Agard et al. | |
| 2014/0236087 A1 * | 8/2014 | Alderete, Jr. | A61M 5/1452 604/152 |
| 2015/0119797 A1 | 4/2015 | Cabiri | |
| 2015/0126926 A1 * | 5/2015 | Giambattista | A61M 5/158 604/135 |
| 2015/0141920 A1 | 5/2015 | O'Connor et al. | |
| 2015/0209505 A1 | 7/2015 | Hanson et al. | |
| 2015/0217045 A1 | 8/2015 | Bente, IV et al. | |
| 2015/0297827 A1 | 10/2015 | Hanson et al. | |
| 2018/0055995 A1 | 3/2018 | Hanson et al. | |

FOREIGN PATENT DOCUMENTS

| | | |
|---|---|---|
| EP | 1427471 B1 | 2/2008 |
| EP | 1695727 B1 | 7/2008 |
| EP | 1513580 B1 | 3/2009 |
| EP | 2077128 A1 | 7/2009 |
| EP | 2379134 A1 | 10/2011 |
| EP | 2429612 A1 | 3/2012 |
| EP | 2433663 A1 | 3/2012 |
| EP | 3028727 B1 | 6/2016 |
| GB | 2166497 A | 5/1986 |
| GB | 2452286 A | 3/2009 |
| JP | S62217975 | 9/1987 |
| JP | 2002050312 A | 1/2002 |
| JP | 2004195227 A | 7/2004 |
| JP | 2005-537112 A | 12/2005 |
| JP | 2009101217 A | 5/2009 |
| JP | 2010527255 A | 8/2010 |
| JP | 2010538799 A | 12/2010 |
| JP | 2010540156 A | 12/2010 |
| JP | 2011-523873 A | 8/2011 |
| WO | WO9856439 A1 | 12/1998 |

(56) References Cited

FOREIGN PATENT DOCUMENTS

| WO | WO1999020327 A2 | 4/1999 |
| WO | WO1999048546 A1 | 9/1999 |
| WO | WO2002028455 A | 4/2002 |
| WO | WO2003/024504 A2 | 3/2003 |
| WO | WO2003103763 A1 | 12/2003 |
| WO | WO2004/062714 A1 | 7/2004 |
| WO | WO2005/037350 A2 | 4/2005 |
| WO | WO2007128767 A1 | 11/2007 |
| WO | WO2008024808 A2 | 2/2008 |
| WO | WO2008142394 A1 | 11/2008 |
| WO | WO2009039214 A1 | 3/2009 |
| WO | WO 2009/125582 A1 | 10/2009 |
| WO | 2009/149547 A1 | 12/2009 |
| WO | WO2010029054 A1 | 3/2010 |
| WO | WO2010077807 A1 | 7/2010 |
| WO | WO2010084113 A1 | 7/2010 |
| WO | WO2010085338 A1 | 7/2010 |
| WO | WO2010112376 A1 | 10/2010 |
| WO | WO2010112377 A1 | 10/2010 |
| WO | WO2010/132196 A1 | 11/2010 |
| WO | WO2011/006652 A1 | 1/2011 |
| WO | WO2011046950 A1 | 4/2011 |
| WO | WO2011090956 A2 | 7/2011 |
| WO | WO 2011/133823 A1 | 10/2011 |
| WO | WO2011121023 A1 | 10/2011 |
| WO | WO2012032411 A2 | 3/2012 |
| WO | 20120085029 A1 | 6/2012 |
| WO | WO2012131044 A1 | 10/2012 |
| WO | WO2013/033421 A2 | 3/2013 |
| WO | WO2013/040032 A | 3/2013 |
| WO | WO 2013/040032 A1 | 3/2013 |
| WO | WO2013/153041 A2 | 3/2013 |
| WO | WO2013033467 A2 | 3/2013 |
| WO | W02013153041 | 10/2013 |
| WO | WO2013/156224 A1 | 10/2013 |
| WO | WO 2014/036239 A2 | 3/2014 |
| WO | WO2014116274 A1 | 7/2014 |
| WO | WO 2016/049501 A1 | 3/2016 |
| WO | WO 2017/177094 A2 | 10/2017 |
| WO | WO 2019/043423 A1 | 3/2019 |

OTHER PUBLICATIONS

NonFinal Office Action, U.S. Appl. No. 14/423,599, entitiled, "Controlled Delivery Drive Mechanisms for Drug Delivery Pumps," (dated Jul. 31, 2017) 6 pages.

Notice of Allowance, U.S. Appl. No. 14/423,599, entitiled, "Controlled Delivery Drive Mechanisms for Drug Delivery Pumps," (dated Jan. 31, 2018) 7 pages.

International Preliminary Report on Patentability for Int'l Application No. PCT/US2013/057367, titled: Controlled Delivery Drive Mechanisms for Drug Delivery Pumps, dated Mar. 3, 2015, 7 pages.

International Search Report and Written Opinion dated Nov. 29, 2017 for International Application No. PCT/IB2017/001047, entitled: "Controlled Delivery Drive Mechanisms for Drug Delivery Pumps."

Notice of Allowance for U.S. Appl. No. 14/423,599, "Controlled Delivery Drive Mechabnisms for Drug Delivery Pumps," dated Jun. 12, 2018.

* cited by examiner

CONTROLLED DELIVERY DRIVE MECHANISMS FOR DRUG DELIVERY PUMPS

CROSS-REFERENCE TO RELATED APPLICATIONS

This application is a divisional of U.S. application Ser. No. 14/423,599, filed on Feb. 24, 2015, which is the U.S. National Stage of International Application No. PCT/US2013/057367, filed on Aug. 29, 2013, which designates the U.S., published in English, and which claims priority to U.S. Provisional Application No. 61/694,534, filed on Aug. 29, 2012; U.S. Provisional Application No. 61/731,744, filed on Nov. 30, 2012; and U.S. Provisional Application No. 61/748,667, filed on Jan. 3, 2013 which are included by reference herein in their entirety for all purposes.

FIELD

This invention relates to drug delivery pumps. More particularly, this invention relates to drive mechanisms for the controlled delivery of drug substances, drug delivery pumps with such drive mechanisms, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The present invention provides drive mechanisms for the controlled delivery of drug substances, drug delivery pumps with such drive mechanisms, the methods of operating such devices, and the methods of assembling such devices. Notably, the drive mechanisms of the present invention control the rate of drug delivery by metering, providing resistance, or otherwise preventing free axial translation of the plunger seal utilized to force a drug substance out of a drug container. The novel embodiments of the present invention thus are capable of delivering drug substances at variable rates. The drive mechanisms of the present invention may be pre-configurable or dynamically configurable, such as by control by the power and control system, to meet desired delivery rates or profiles, as explained in detail below. Additionally, the drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. Because the end-of-dose indication is related to the physical end of axial translation of one or more components of the drive mechanism, the drive mechanism and drug pump provide a true end-of-dose indication to the user. Through these mechanisms, confirmation of drug dose delivery can accurately be provided to the user or administrator. Accordingly, the novel devices of the present invention alleviate one or more of the problems associated with prior art devices, such as those referred to above.

In a first embodiment, the present invention provides a controlled delivery drive mechanism which includes a drug container having a barrel and a plunger seal; a drive housing within which at least initially partially resides a piston having an interface surface and a drive rack; and a power spring coupled, directly or indirectly, to a drive pinion which interfaces with drive rack of the piston to convert rotational movement of power spring and the drive pinion to axial translation of the drive rack. The piston is configured to contact and axially translate the plunger seal within barrel. This configuration converts rotational movement of the drive pinion to axial translation of the drive rack. A regulating mechanism meters the drive pinion such that the piston is axially translated at a controlled rate. The drug container may contain a drug fluid within a drug chamber for drug delivery at a controlled rate.

In another embodiment, the present invention provides a controlled delivery drive mechanism having a drug container having a barrel and a plunger seal; a drive housing within which at least initially partially resides a linear power spring and a piston having an interface surface and a drive rack, wherein the linear power spring is coupled, directly or indirectly, to the piston to convert axial force of the linear power spring into torsional motion of a drive pinion. The piston is configured to contact and axially translate the plunger seal within barrel. A regulating mechanism meters the drive pinion such that the piston is axially translated by the linear power spring at a controlled rate.

In at least one embodiment, the regulating mechanism is an escapement regulating mechanism coupled to, or acting with, the power spring. The escapement regulating mechanism further includes a gear train having one or more gears, a rotation shaft, and a gear transmission having one or more gears, wherein at least one gear of the gear transmission is capable of engaging the drive pinion such that rotation of the gear causes rotation of the drive pinion. In a particular embodiment, the escapement regulating element further includes a lever and an escape wheel configured to engage and meter the rotational movement of the gear train. The lever has pins and a prong, wherein the prong movably engages a post and is configured to removably engage an impulse pin of a balance wheel, and wherein the balance wheel engages and is capable of oscillating around a post in combination with a hair spring. The escape wheel is a compound gear having escape teeth around the circumference of a large diameter escape gear and a small diameter gear configured to engage and meter the gear train. The metering of the drive pinion and/or the gear train by an escapement regulating mechanism controls the rate or profile of drug delivery to a user.

In at least one embodiment, the drive mechanism utilizes a status reader configured to read or recognize one or more corresponding status triggers, wherein, during operation of the drive mechanism, interaction between the status reader and the status triggers transmit a signal to a power and control system to provide feedback to a user. The status reader may be an optical status reader and the corresponding status triggers are gear teeth of a drive gear, a mechanical status reader and the corresponding status triggers are gear teeth of the drive gear, a mechanical status reader and the corresponding status triggers are external features of the piston and/or drive rack, or an optical status reader and the corresponding status triggers are external features of the piston and/or drive rack.

In a further embodiment, the present invention provides a drug delivery pump having a controlled delivery drive mechanism. The drug pump includes a housing and an assembly platform, upon which an activation mechanism, an insertion mechanism, a fluid pathway connection, a power and control system, and the controlled delivery drive mechanism may be mounted. The drug container of the drug pump contains a drug fluid within a drug chamber for drug delivery at a controlled rate.

The drug pump may utilize the first controlled delivery drive mechanism described above in the first embodiment, which configuration utilizes a power spring and converts rotational movement of the drive pinion to axial translation of the drive rack, or the second controlled delivery drive mechanism described above in the second embodiment, which configuration utilizes a linear power spring to convert axial force into torsional motion of a drive pinion. In either embodiment, the piston is configured to contact and axially translate the plunger seal within barrel. Each embodiment may also utilize a regulating mechanism to meter the drive pinion such that the piston is axially translated by the linear power spring at a controlled rate.

In at least one embodiment, the regulating mechanism is an escapement regulating mechanism coupled to, or acting with, the power spring. The escapement regulating mechanism further includes a gear train having one or more gears, a rotation shaft, and a gear transmission having one or more gears, wherein at least one gear of the gear transmission is capable of engaging the drive pinion such that rotation of the gear causes rotation of the drive pinion. In a particular embodiment, the escapement regulating element further includes a lever and an escape wheel configured to engage and meter the rotational movement of the gear train. The lever has pins and a prong, wherein the prong movably engages a post and is configured to removably engage an impulse pin of a balance wheel, and wherein the balance wheel engages and is capable of oscillating around a post in combination with a hair spring. The escape wheel is a compound gear having escape teeth around the circumference of a large diameter escape gear and a small diameter gear configured to engage and meter the gear train. The metering of the drive pinion and/or the gear train by an escapement regulating mechanism controls the rate or profile of drug delivery to a user.

In at least one embodiment, the drug pump utilizes a status reader configured to read or recognize one or more corresponding status triggers, wherein, during operation of the drive mechanism, interaction between the status reader and the status triggers transmit a signal to a power and control system to provide feedback to a user. The status reader may be an optical status reader and the corresponding status triggers are gear teeth of a drive gear, a mechanical status reader and the corresponding status triggers are gear teeth of the drive gear, a mechanical status reader and the corresponding status triggers are external features of the piston and/or drive rack, or an optical status reader and the corresponding status triggers are external features of the piston and/or drive rack.

The novel embodiments of the present invention provide drive mechanisms which are capable of metering, providing resistance, or otherwise preventing free axial translation of the plunger seal utilized to force a drug substance out of a drug container and, thereby, controlling the rate of delivery of drug substances. The novel controlled delivery drive mechanisms are additionally capable of providing the incremental status of the drug delivery before, during, and after operation of the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. For example, the embodiments may include one or more batteries utilized to power the motor, drive mechanisms, and drug pumps of the present invention. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein.

DETAILED DESCRIPTION

Figure 1A:
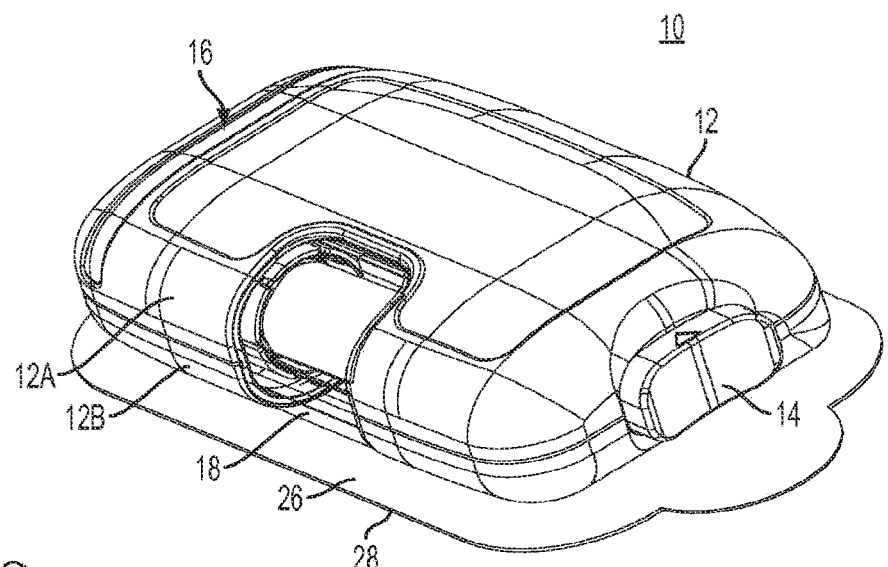
FIG. 1A shows an isometric view of a drug delivery pump having a variable rate controlled delivery drive mechanism, according to one embodiment of the present invention.

The present invention provides drive mechanisms for the controlled delivery of drug substances and drug delivery pumps which incorporate such drive mechanisms. The drive mechanisms of the present invention control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the variable rate drive mechanism and drug pump may provide an end-of-dose indication.

As used herein to describe the drive mechanisms, drug delivery pumps, or any of the relative positions of the components of the present invention, the terms "axial" or "axially" refer generally to a longitudinal axis "A" around which the drive mechanisms are preferably positioned, although not necessarily symmetrically there-around. For clarity, the accompanying figure drawings also utilize an axis "B" which is perpendicular to axis "A". The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the drug pumps. According to various aspects and embodiments described herein, reference is made to a "biasing member", such as in the context of one or more biasing members for asserting force on a plunger seal. It will be appreciated that the biasing member may be any member that is capable of storing and releasing energy. Non-limiting examples include a spring, such as for example a coiled spring, a compression or extension spring, a torsional spring, or a leaf spring, a resiliently compressible or elastic band, or any other member with similar functions. In at least one embodiment of the present invention, the biasing member utilized by the drive mechanisms is a spring, preferably a torsional or power spring.

The novel devices of the present invention provide variable rate controlled delivery drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pumps, drive mechanisms, and their respective components are described further herein with reference to the accompanying figures.

Figure 1B:
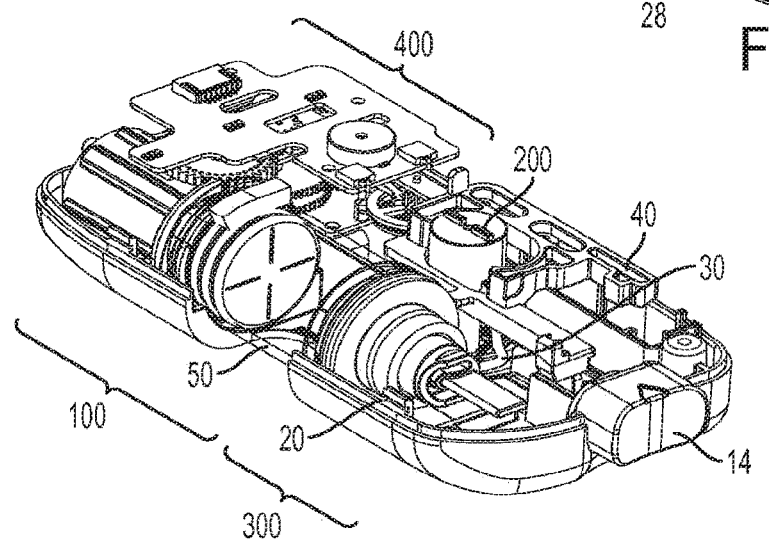
FIG. 1B shows an isometric view of the interior components of the drug delivery pump shown in FIG. 1A (shown without the adhesive patch)
Figure 1C:
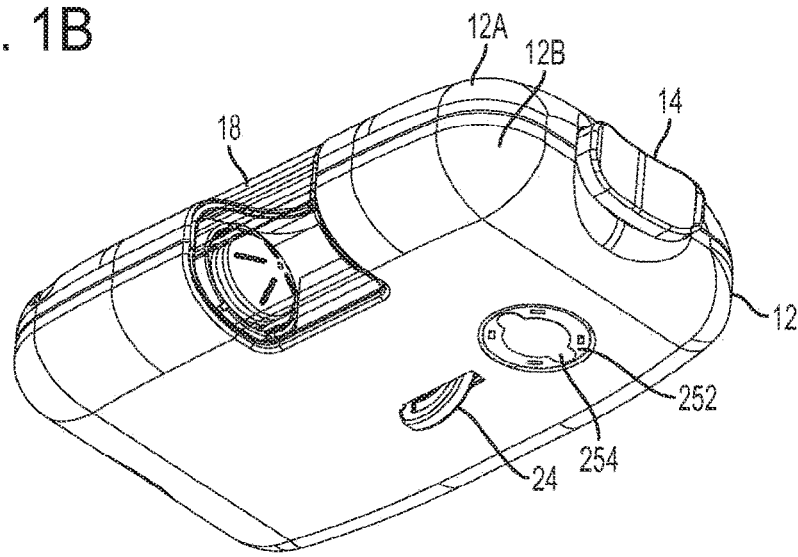
FIG. 1C shows an isometric view of the bottom of the drug delivery pump shown in FIG. 1A (shown without the adhesive patch)

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device or drug pump according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump further includes assembly platform 20, sterile fluid conduit 30, drive mechanism 100 having drug container 50, insertion mechanism 200, fluid pathway connection 300, and power and control system 400. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the body of the user. Housing 12 is described in further detail hereinafter with reference to other components and embodiments of the present invention.

Drug pump is configured such that, upon activation by a user by depression of the activation mechanism, the drug pump is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIG. 1C) may be provided in one embodiment as a safety feature to ensure that the power and control system 400, or the activation mechanism, cannot be engaged unless the drug pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system 400 will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14. During the drug delivery process, the power and control system 400 is configured to provide a dispensing status signal via the status indicator 16. After the drug has been administered into the body of the user and after the end of any additional dwell time, to ensure that substantially the entire dose has been delivered to the user, the power and control system 400 may provide an okay-to-remove status signal via the status indicator 16. This may be independently verified by the user by viewing the drive mechanism and drug dose delivery through the window 18 of the pump housing 12. Additionally, the power and control system 400 may be configured to provide one or more alert signals via the status indicator 16, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Fluid Pathway Connection:

A number of fluid pathway connections may be utilized within the embodiments of the present invention. Generally, a suitable fluid pathway connection includes a sterile fluid conduit, a piercing member, and a sterile sleeve attached to a drug container or a sliding pierceable seal integrated within a drug container. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In one such embodiment, the fluid pathway connection may be substantially similar to that described in International Patent Application No. PCT/US2012/054861, which is included by reference herein in its entirety for all purposes. According to such an embodiment, the connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connection may be integrated into a drug container as described in International Patent Application No. PCT/US2013/030478, for example, which is included by reference herein in its entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The sliding pierceable seal is caused to slide towards the cap, causing it to be pierced by the piercing member retained within the integrated sterile fluid pathway connection. Accordingly, the integrated sterile fluid pathway connection is connected (i.e., the fluid pathway is opened) by the combination pneumatic/hydraulic force of the air/gas and drug fluid within the drug chamber created by activation of a drive mechanism. Once the integrated sterile fluid pathway connection is connected or opened, drug fluid is permitted to flow from the drug container, through the integrated sterile fluid pathway connection, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

Regardless of the fluid pathway connection utilized by the drug pump, the drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Insertion Mechanism:

A number of insertion mechanisms may be utilized within the drug pumps of the present invention. The pump-type delivery devices of the present invention may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present invention.

In at least one embodiment, the insertion mechanism 200 includes an insertion mechanism housing having one or more lockout windows, and a base for connection to the assembly platform and/or pump housing (as shown in FIG. 1B and FIG. 1C). The connection of the base to the assembly platform 20 may be, for example, such that the bottom of the base is permitted to pass-through a hole in the assembly platform to permit direct contact of the base to the body of the user. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit 30 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 254 (shown in FIG. 1C).

According to at least one embodiment of the present invention, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. As shown in FIG. 1B, the lockout pin(s) 208 may be directly displaced by user depression of the activation mechanism 14. As the user disengages any safety mechanisms, such as an optional on-body sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows 202A of insertion mechanism housing 202. Displacement of the lockout pin(s) 208 permits insertion biasing member to decompress from its initial compressed, energized state. This decompression of the insertion biasing member drives the needle and the cannula into the body of the user. At the end of the insertion stage, the retraction biasing member is permitted to expand in the proximal direction from its initial energized state. This axial expansion in the proximal direction of the retraction biasing member retracts the needle, while maintaining the cannula in fluid communication with the body of the user.

Accordingly, the insertion mechanism may be used to insert a needle and cannula into the user and, subsequently, retract the needle while retaining the cannula in position for drug delivery to the body of the user.

Figure 2:
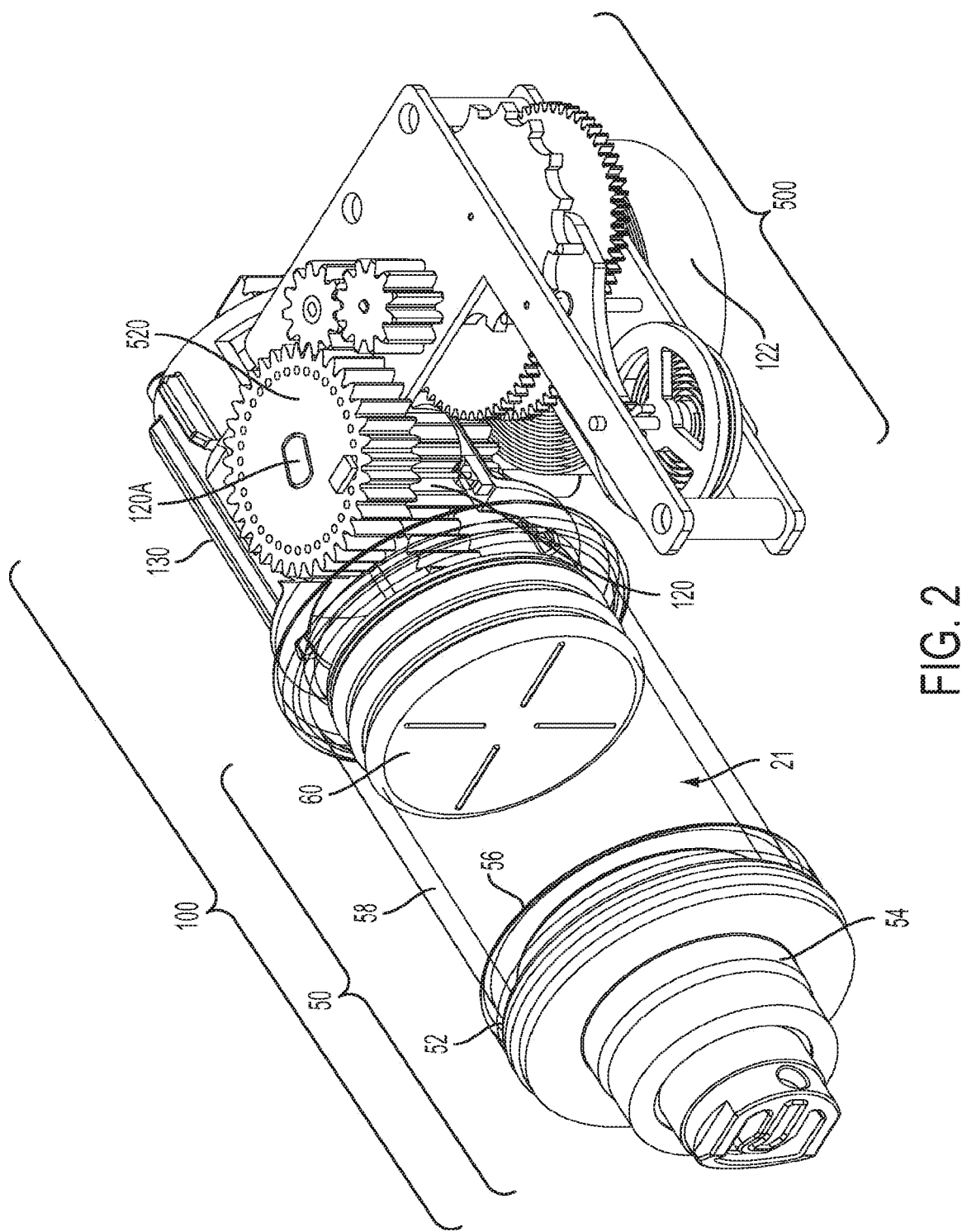
FIG. 2 shows an isometric view of a controlled delivery drive mechanism, according to at least one embodiment of the present invention.

Drive Mechanism:

With reference to the embodiments shown in FIGS. 2 and 3, drive mechanism 100 includes a drive housing 130, and a drug container 50 having a cap 52, a pierceable seal 56, a barrel 58, and a plunger seal 60. A drug chamber 21, located within the barrel 58 between the pierceable seal and the plunger seal 60, may contain a drug fluid for delivery through the insertion mechanism and drug pump into the body of the user. The seals described herein may be comprised of a number of materials but are, in a preferred embodiment, comprised of one or more elastomers or rubbers. The drive mechanism may further include a connection mount 54 to guide the insertion of the piercing member of the fluid pathway connection into the barrel 58 of the drug container 50. The drive mechanism 100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connection, for delivery through the fluid pathway connection, sterile fluid conduit, and insertion mechanism into the body of the user.

In one particular embodiment, the drive mechanism 100 employs one or more springs as the drive biasing member(s). Upon activation of the drug pump by the user, the power and control system may be actuated to directly or indirectly release the spring(s) from an energized state. Upon release, the spring(s) may be utilized, directly or indirectly, to drive the plunger seal and force the fluid drug out of the drug container. More specifically, the spring may be utilized, directly or indirectly, to drive a piston which, in turn, acts upon the plunger seal to force the fluid drug out of the drug container. The fluid pathway connection may be connected through the pierceable seal prior to, concurrently with, or after activation of the drive mechanism to permit fluid flow from the drug container, through the fluid pathway connection, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

Referring now to the embodiment of the drive mechanism shown in FIG. 2 and FIG. 3, the drive mechanism 100 includes a drug container 50 having a cap 52, a pierceable seal 56, a barrel 58, and a plunger seal 60, and optionally a connection mount 54. The drug container 50 is mounted to a distal end of a drive housing 130. A piston 110 having an interface surface 110C and a drive rack 110A is retained at least partially within the drive housing 130, between the drug container 50 and the proximal end of the housing 130. Optionally, a cover sleeve may be utilized to engage the piston 110 and cover the drive rack 110A to hide such components from user view upon expansion from its initial position. The cover sleeve may be configured to engage and slide upon the piston 110, between the piston 110 and the distal end of the drive mechanism housing 130 to hide the drive rack 110A from user view upon expansion from its initial energized state.

Figure 3A:
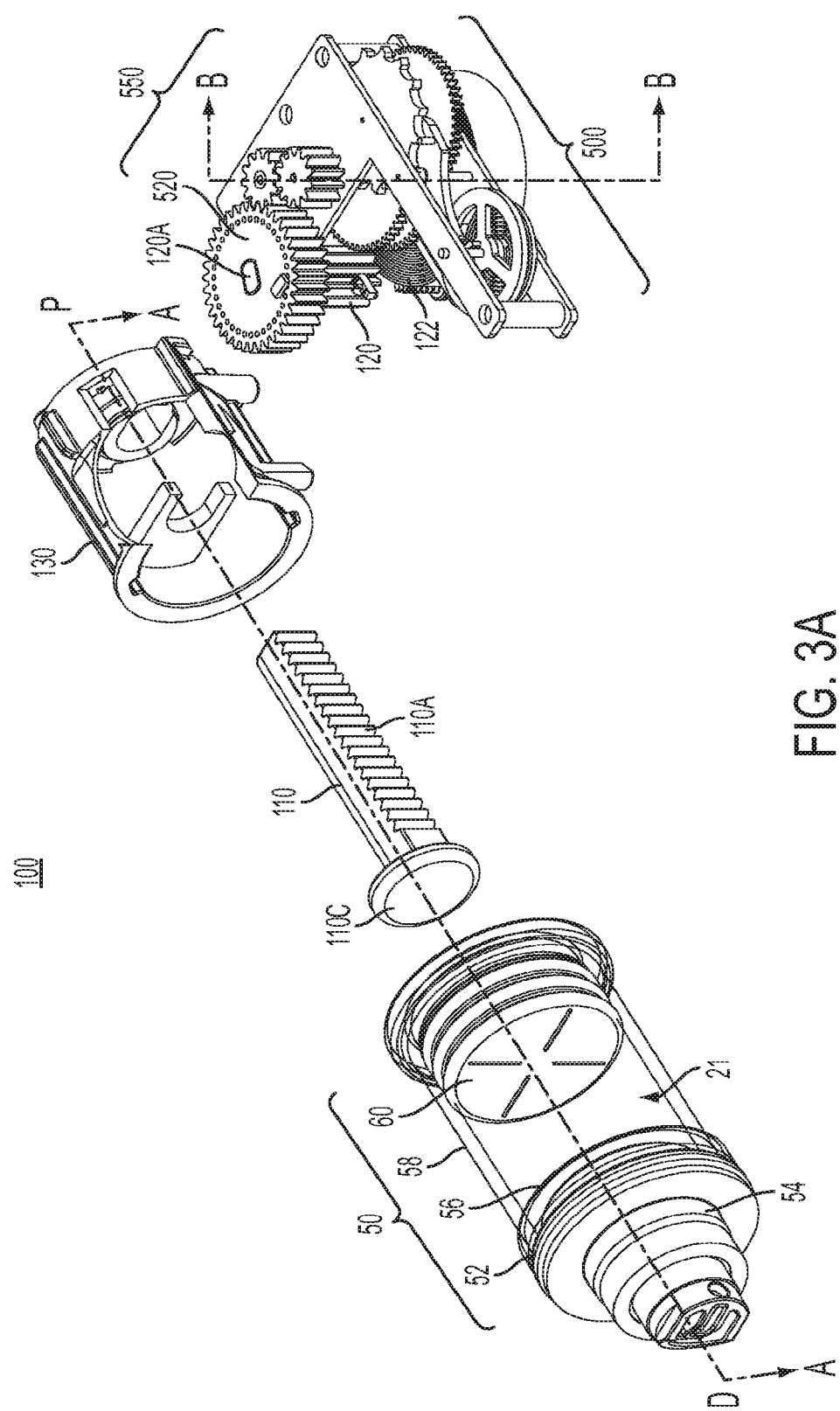
FIG. 3A shows a partially exploded view, along an axis "A," of the drive mechanism shown in FIG. 2.
Figure 3B:
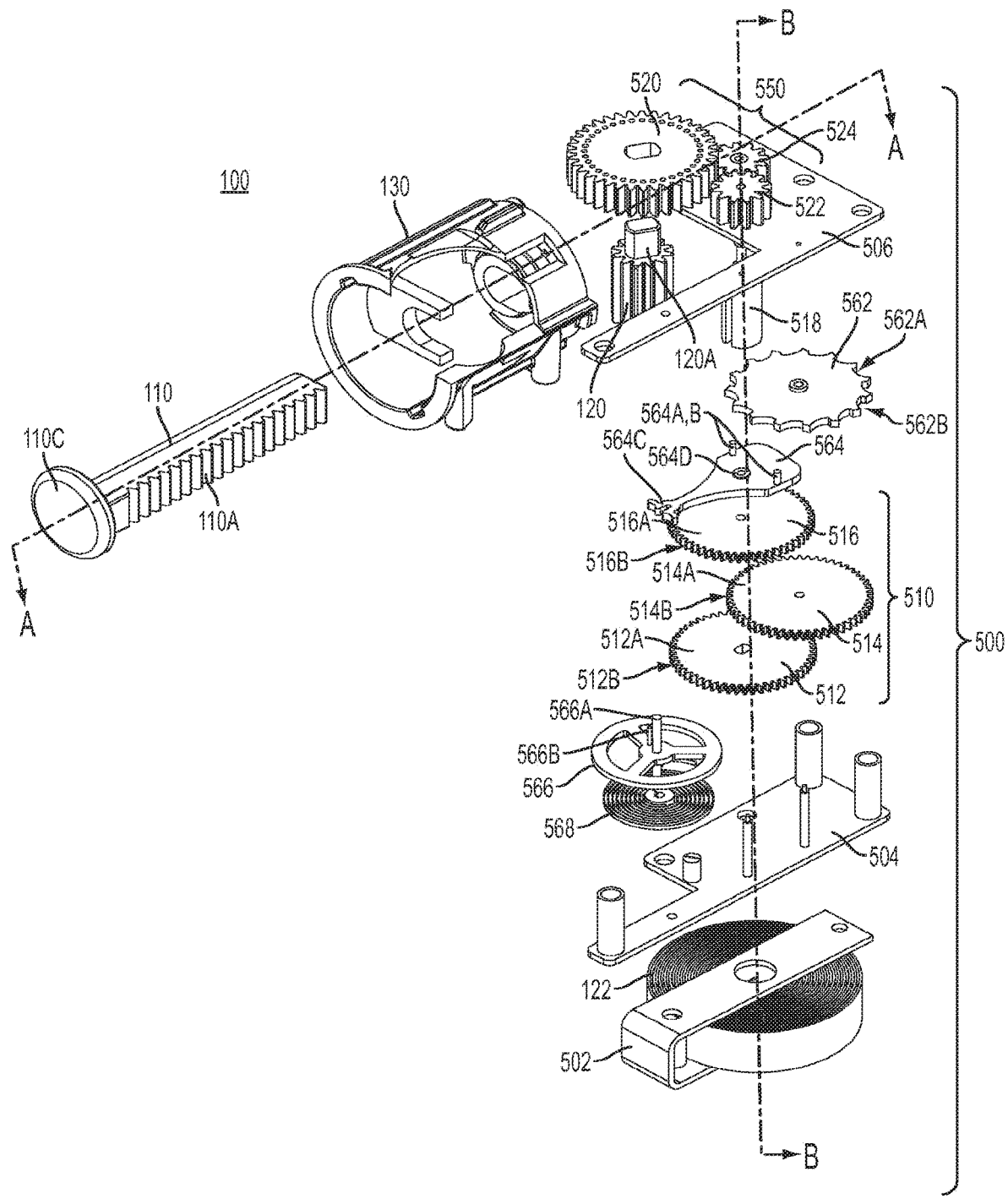
FIG. 3B shows a fully exploded view, along an axis "A" and along a perpendicular axis "B", of certain components of the drive mechanism shown in FIG. 2.
Figure 8:
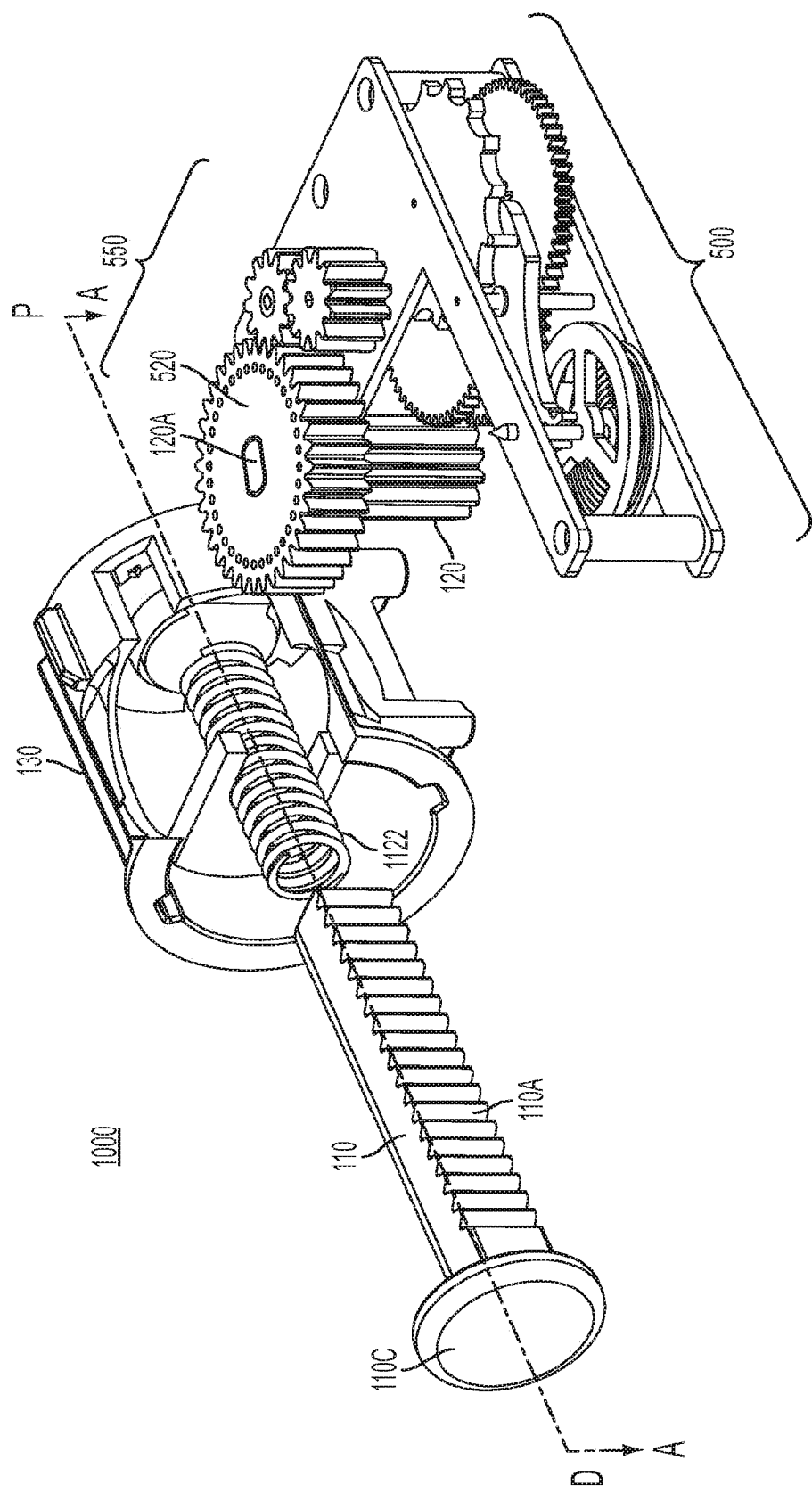
FIG. 8 shows an isometric view of a controlled delivery drive mechanism according to another embodiment of the present invention.

As shown in FIGS. 3A and 3B, the controlled delivery drive mechanism 100 of the present invention may utilize a power spring 122 coupled, directly or indirectly to the drive pinion 120 which interfaces with drive rack 110A of the piston 110 to convert rotational movement of the drive pinion 120 to axial translation of the drive rack 110A, thereby pushing plunger seal 60 within barrel 58 to force a fluid from drug chamber 21. Notably, the power spring 122 imparts torque to a gear assembly, such as the drive pinion 120, which pushes a plunger seal 60 within barrel 58 which contains the drug substance. Alternatively a linear power spring 1122 can be coupled directly or indirectly to the piston 110 with drive rack 110A to convert axial force into torsional motion which is coupled to drive pinion 120 and into the regulating mechanism 500, as shown in FIG. 8. In both configurations, the plunger seal 60 advances into the drug container 50, the drug substance is dispensed through the sterile pathway connection 300, conduit 30, insertion mechanism 200, and into the body of the user for drug delivery. Certain reaction forces on the plunger seal, such as hydraulic resistance from the flow of the drug substance and friction of the plunger seal against the barrel, can vary significantly. As such, it is desirable to have a regulating mechanism 500 in the drive mechanism 100 which keeps a constant rate of delivery as these forces vary. In the embodiments of the present invention, the regulating mechanism 500 is an escapement regulating mechanism. The escapement regulating mechanism retards or restrains the gear assembly, only allowing it to advance at a regulated or desirable rate. In such a configuration, the power spring 122 is designed to supply sufficient torque to overcome worst case variations in the hydraulic and frictional forces. In theory, any excess force which occurs under more nominal reaction force conditions is absorbed by the escapement regulating mechanism and the delivery rate remains constant.

In at least one embodiment of the present invention, the drive mechanism 100 utilizes an escapement regulating element 500 and a power spring 122. The power spring 122 is configured to provide rotational movement, around an axis "B", to one or more gears 512, 514, 516 of a gear train 510 (and/or to gear 522 of gear transmission 550). Each of the gears 512, 514, 516 may be, for example, compound gears having a small diameter gear attached at a shared center point to a large diameter gear. For example first compound gear 512 has small diameter gear 512B (not visible) attached to large diameter gear 512A. The small diameter gear of each compound gear engages the large diameter gear, for example, of the next compound gear in the gear train 510 such that rotational movement of the first compound gear 512 is conveyed by engagement of the gears (such as by engagement of corresponding gear teeth) to the second compound gear 514, and so on through the gear train 510. Such rotational movement of the gear train 510 may be conveyed by a rotation shaft 518 to a gear transmission 550 having one or more gears, including drive gear 520. For example, the gear transmission 550 may include gear 522 and gear 524 in addition to drive gear 520. The drive gear 520 is connected to drive pinion 120 (such as by connection protrusion 120A) such that rotation of the drive gear 520 causes rotation of the drive pinion 120. The drive pinion 120 is configured to engage the drive rack 110A of the piston 110 to convert rotational movement of the drive pinion 120 to axial translation of the drive rack 110A, thereby pushing plunger seal 60 within barrel 58 to force a fluid from drug chamber 21. The rotational movement of the drive gear 520, and thus the axial translation of the drive rack 110A and plunger seal 60, are metered, restrained, or otherwise prevented from free axial translation by other components of the escapement regulating element 500, as described herein.

In at least one embodiment of the present invention, the rotation shaft 518 is keyed to both the first compound gear 512 and the first gear 522 of the gear transmission 550. This configuration permits rotational movement of the first compound gear 512, which is in direct rotational alignment and/or relationship with the power spring 122, to be keyed and cause power transfer and rotation of the gear transmission 550 (such as at gear 522). In this configuration, at least some of power from the power spring 122 is directed for use in axially translating the drive rack 110A of the piston 110 and the plunger seal 60; while at least a portion of the power from the power spring 122 is directed for use by the escape wheel 562, balance wheel 566, hair spring 568, and lever 564 components of the escapement regulating element 500. Accordingly, while the power spring provides force used for axial translation of the plunger seal 60, it also powers the escapement regulating element 500 which functions to meter or restrain the force provided for such axial translation. The compound gear structure of the gear train 510 permits the splitting of the force provided by the power spring 122. Some of the power from the power spring 122 is transferred directly to gear 522, rotation shaft 518, and first gear 522 of the gear transmission 550; while some of the power is transferred to gear 514, gear 516, lever 564, and escape wheel 562, for regulation or metering by interaction with the balance wheel 566 and hair spring 568, to permit a small diameter gear 562B of the escape wheel 562 to regulate or meter the gear train 510.

The escapement regulating element 500 further includes an escape wheel 562 and a lever 564. The escape wheel 562 is a compound gear having escape teeth around the circumference of a large diameter escape gear 562A and a small diameter gear 562B (not visible) configured to engage the gear train 510 and meter, restrain, or otherwise prevent free rotational movement thereof. The lever 564 has pins 564A,B and prong 564C. Prong 564C movably engages a post 566A and is configured to removably engage an impulse pin 566B of a balance wheel 566. The balance wheel 566 engages and functions as an oscillator around a pivot point 564D in combination with a hair spring 568. The power spring 122 may be retained or braced within a winder 502 in a manner that permits the power spring 122 to rotationally move freely within the winder 502. The gear train 510, escape wheel 562, balance wheel 566, hair spring 568, and lever 564 may be mounted on and able to freely rotate or move on a plate 504. Similarly, gear transmission 550 may be mounted on and able to freely rotate on a platform 506. The winder 502, plate 504, and platform 506 may utilize one or more spacer columns to maintain the desired spacing between components and one or more pivot pins upon which the components may be mounted and freely rotated.

Figure 4A:
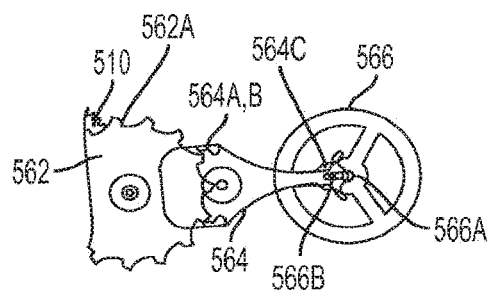
FIGS. 4A-4C shows an enlarged view of an escapement regulating mechanism of a drive mechanism, according to at least one embodiment of the present invention.
Figure 4B:
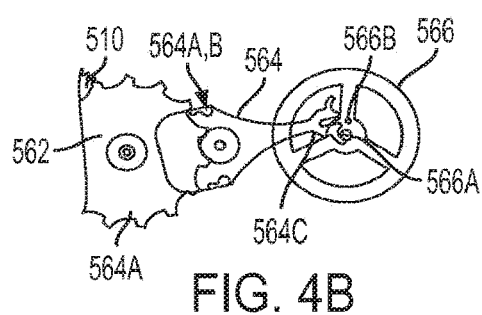
Figure 4C:
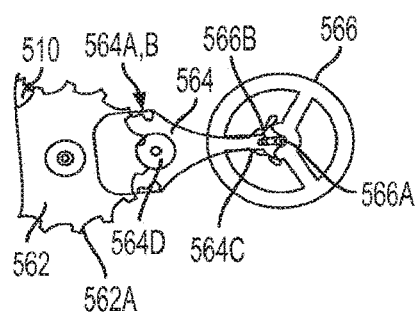
Figure 4D:
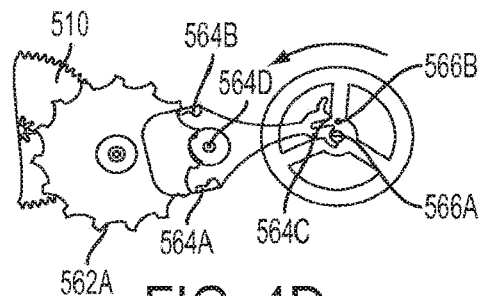
FIGS. 4D-4H shows the progression of the escapement regulating mechanism, according the embodiment shown in FIGS. 4A-4C, during operation.
Figure 4E:
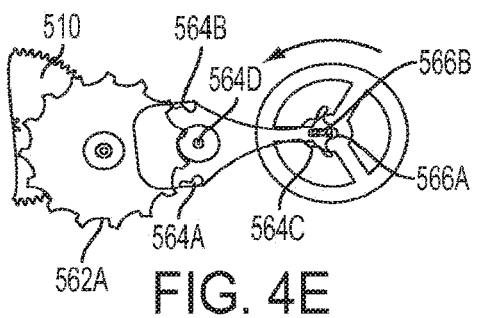
Figure 4F:
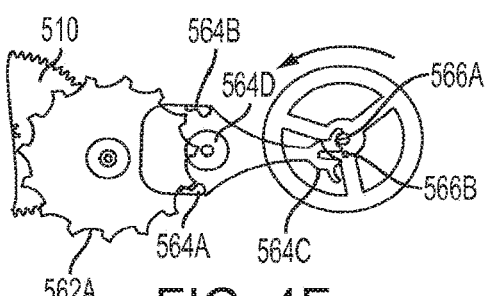
Figure 4G:
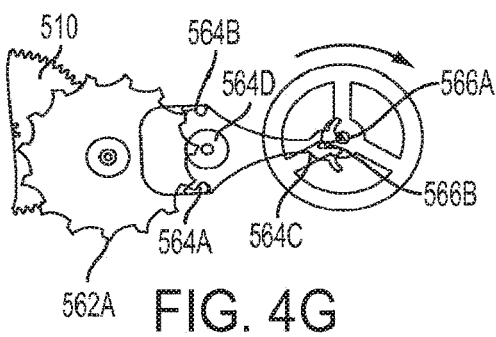
Figure 4H:
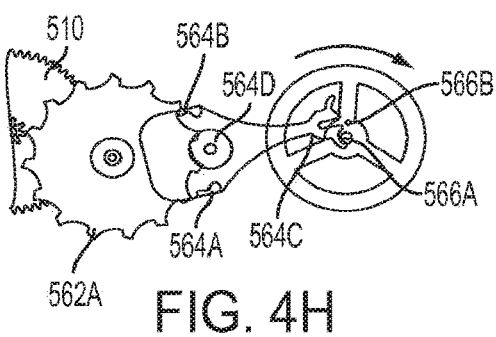

The function of the escape wheel 562, balance wheel 566, hair spring 568, and lever 564 components of the escapement regulating element 500 are explained with reference to FIG. 3B and FIGS. 4A-4H. The escape wheel 562 is a compound gear having escape teeth around the circumference of a large diameter escape gear 562A and a small diameter gear 562B (not visible) configured to engage the gear train 510 and meter, restrain, or otherwise prevent free rotational movement thereof. The lever 564 has pins 564A,B and prong 564C. Prong 564C movably engages a post 566A and is configured to removably engage an impulse pin 566B of a balance wheel 566. The balance wheel 566 engages and functions as an oscillator around a pivot point 564D in combination with a hair spring 568. The escape wheel 562 and lever 564 may initially be in an activation position, as shown in FIG. 4A. The escape wheel 562 and lever 564 generally function to perform two steps, termed the locking action and the impulse action. These two actions are illustrated in FIG. 4B and FIG. 4C, respectively, and in which the gear train 510 is applying a clockwise torque on the escape wheel 562. In the locking action, one of two lever pins 564A,B blocks escape wheel 562 rotation on the radial face of a tooth on the escape gear 562A. This locks the gear train 510 between impulse actions. In the impulse action, a lever pin 564A,B slides up to this tooth face due to action of the balance wheel 566 on the lever 564. The escape wheel becomes unlocked and does mechanical work on the lever pin 564A, B via a sliding action, which in turn imparts kinetic energy to the balance wheel 566. The lever 564 pivots upon a pivot point 564D until the opposite pin 564A,B engages with an escape wheel tooth on the escape gear 562A, and the locked state is re-entered after a half tooth advance of the escape wheel 562. The transition from locking action to impulse action is triggered by the balance wheel 566, which functions as an oscillator in combination with the hair spring 568. It cycles at a natural frequency that serves as the rate control. The balance wheel 566 contains an impulse pin 566B which interacts with the lever 564 at prong 564C. For the impulse phase depicted in FIG. 4C, a clockwise moment on the lever 564 exerts a counterclockwise moment on the balance wheel 566, adding to its kinetic energy. The balance wheel 566 rotates until its kinetic energy is absorbed by the hair spring 568. It stops, reverses, and reengages the impulse pin 566B with the lever 564. A complete cycle is shown in the transition between FIGS. 4D-4H.

To unlock the escapement regulating mechanism 500, the balance wheel 566 must have enough kinetic energy to drag the lever pin 564A,B up the face of the tooth of the escape gear 562A of the escape wheel 562. If the impulse action adds less energy than is lost to friction, the balance wheel 566 will rotate less and less and finally stall, locking the escapement regulating mechanism 500. If the escapement stops in this way under load, it will not restart easily. To be self-starting, the hair spring 568 must align the lever 564 along the axis connecting the pivot of the escape wheel 562 and the pivot of the balance wheel 566, as shown in FIG. 4A. The lever pins 564A,B will be positioned so that a bevel tooth face can immediately start an impulse action upon application of a drive torque. This alignment can occur only with the escapement regulating mechanism 500 in an unloaded state. The power spring 122 torque must be isolated from the escapement regulating mechanism 500 until the start of delivery. This action may be initiated by a user imparting a force on an activation mechanism and, directly or indirectly through a power and control system 400, applying a drive torque to start the initial impulse action. Once the escapement regulating mechanism 500 is initiated, it can be effectively utilized to meter, restrain, or otherwise prevent free rotational movement of the gear train 510, gear transmission 550, drive gear 520 and drive pinion 120, and, thus, axial translation of the drive rack 110A and plunger seal 60. In a particular embodiment, the escape wheel 562 is a compound gear having escape teeth around the circumference of a large diameter escape gear 562A and a small diameter gear 562B (not visible). The small diameter gear 562B of the escape wheel 562 engages the drive train 510, which engages with gear transmission 550 through rotation shaft 518. This novel configuration directly permits the escape wheel 562 to regulate the rotation of the drive train 510 imparted by the power spring 122, which then efficiently regulates the drive transmission 550, drive gear 520, drive pinion 120, and drive rack 110A of the piston 110.

The novel embodiments of the present invention may be utilized to meter, restrain, or otherwise prevent free rotational movement and, thus, axial translation of the components of the controlled delivery drive mechanism 100. Accordingly, the escapement regulating mechanism 500 only controls the motion of the drive mechanism, but does not apply the force for the drug delivery. One or more additional biasing members, such as compression springs, may be utilized to drive or assist the driving of the piston 110 (as shown in FIG. 8). For example, a compression spring may be utilize within the drive housing 130 for this purpose, with the power spring 122 partly driving the piston 110 and plunger seal 60 and partly driving the escapement regulating element 500 to perform the metering as described above. Accordingly, the means to control flow is separate from the load on the piston 110 and the plunger seal 60. While the power spring 122 applies the force that is utilized to drive the piston 110 and plunger seal 60 for drug delivery, the escapement regulating mechanism 500 only controls, meters, or regulates such action. A mechanical timing system, such as the escapement regulating mechanism described herein, may be utilized to allow the piston 110 and plunger seal 60 to translate axially a controlled distance, or a controlled volume, and may be utilized to meet a desired delivery rate or profile. The timing system can be controlled by quartz timing instead of mechanical timing, as would be appreciated by one having ordinary skill in the art. For quartz timing, a battery provides power to a microchip and circuit. The quartz crystal oscillates at a precise frequency. Alternate electrical timing mechanisms such as, for example, RC timing mechanisms, may also be used, including clock functions commonly found in microprocessors. Depending on the period that the delivery is planned to occur over, the microchip drives a motor based on a number of quartz crystal oscillations or other timing signals. The motor releases motion of a drive train, drive transmission, and/or drive rack, to control the axial translation of a plunger in a similar manner as described herein for the mechanical timing system.

Figure 5A:
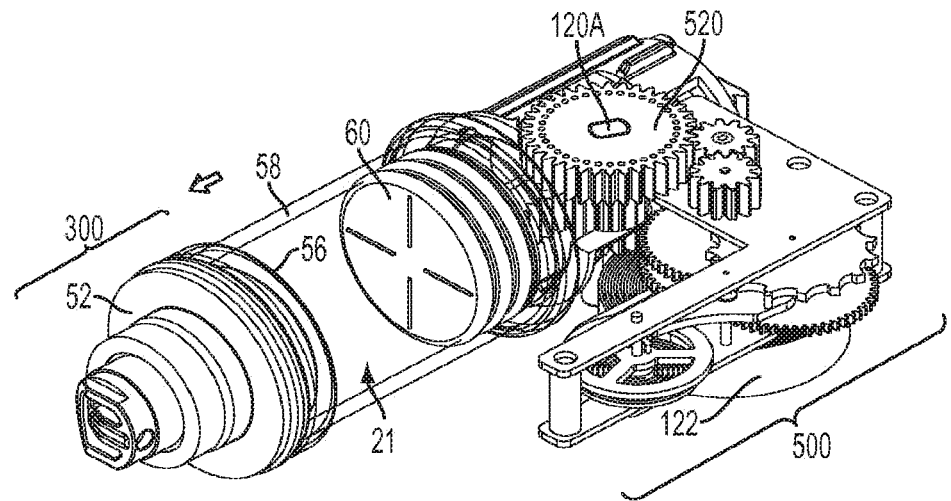
FIG. 5A shows an isometric view of the drive mechanism shown in FIG. 2 in an initial inactive state.
Figure 5B:
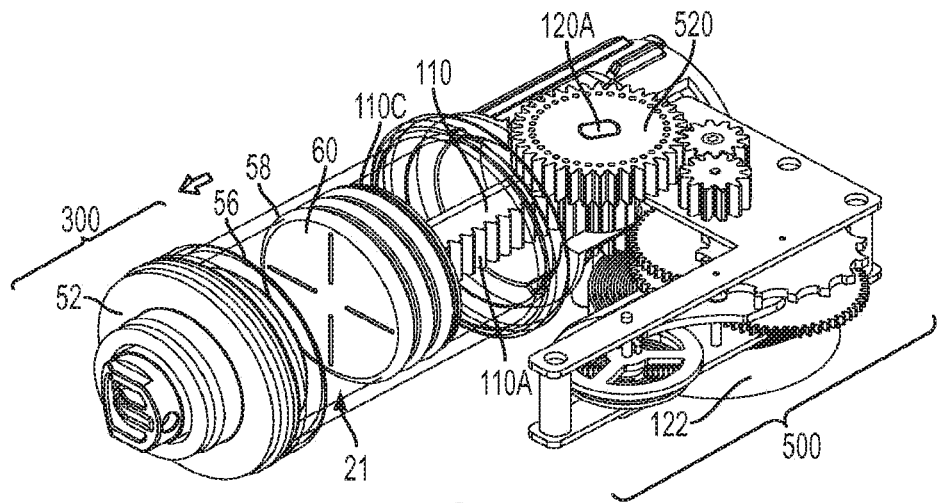
FIG. 5B shows an isometric view of the drive mechanism shown in FIG. 2 in an actuated state as the mechanism controls the rate or profile of drug delivery.
Figure 5C:
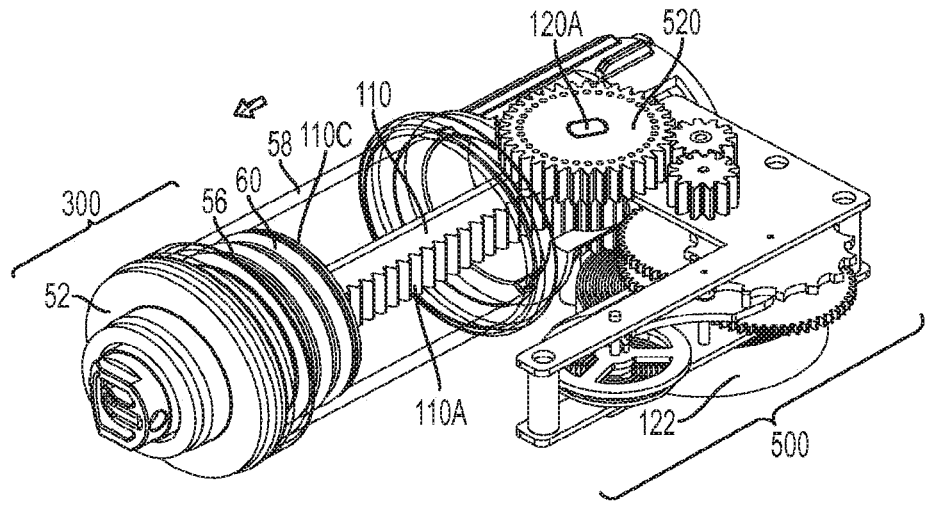
FIG. 5C shows an isometric view of the drive mechanism shown in FIG. 2 as the mechanism completes drug delivery.
Figure 6A:
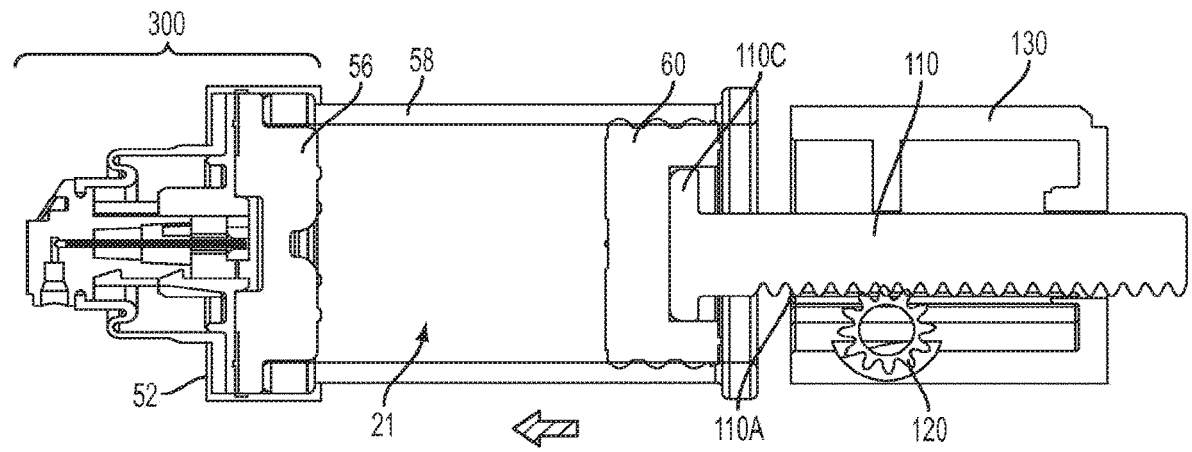
FIG. 6A shows a cross-sectional view of the drive mechanism shown in FIG. 5A in an initial inactive state.
Figure 6B:
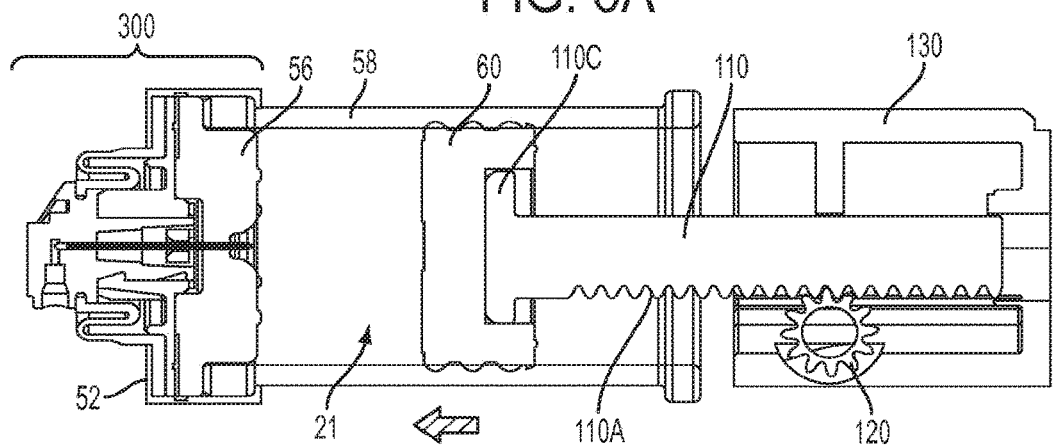
FIG. 6B shows a cross-sectional view of the drive mechanism shown in FIG. 5B in an actuated state as the mechanism controls the rate or profile of drug delivery.
Figure 6C:
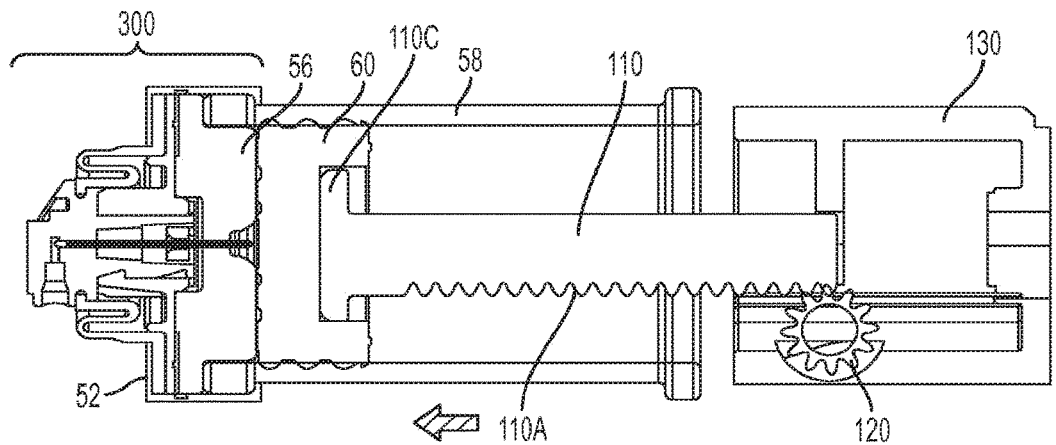
FIG. 6C shows a cross-sectional view of the drive mechanism shown in FIG. 5C as the mechanism completes drug delivery and, optionally, performs a compliance push to ensure completion of drug delivery.

The drive mechanism 100 having an escapement regulating mechanism 500 functions to control the rate of drug delivery forced by the axial translation of a piston 110 and a plunger seal 60 within a barrel 58 of a drug container 50. This is shown in the transition from FIGS. 5A-5C and FIGS. 6A-6C. As described above, the power spring 122 imparts a force to the drive mechanism which is regulated, metered, or otherwise controlled by the escapement regulating mechanism 500 to control the rate of axial translation of the piston 110 and plunger seal 60 for drug delivery. Upon initiation by the user, the power spring 122 is permitted to apply a force or torque to the system which is regulated by the escapement regulating mechanism 500. This causes the drive mechanism shown in FIG. 5A and FIG. 6A to activate and permit metered axial translation of the piston 110 and plunger seal 60 in the distal direction within a barrel 58 (i.e., in the direction of the hatched arrow). This metered activity continues through drug delivery at a controlled rate or drug delivery profile, as shown in FIG. 5B and FIG. 6B, until substantially all of the drug fluid has been dispensed from drug chamber 21 through the sterile pathway connection 300, as shown in FIG. 5C and FIG. 6C.

The components of the drive mechanism 100, upon activation, may be used to drive axial translation in the distal direction of the plunger seal 60 of the drug container 50. Optionally, the drive mechanism 100 may include one or more compliance features which enable additional axial translation of the plunger seal 60 to, for example, ensure that substantially the entire drug dose has been delivered to the user. For example, the plunger seal 60, itself, may have some compressibility permitting a compliance push of drug fluid from the drug container. The plunger seal 60, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Similarly, an optional cover sleeve may be utilized to hide the visibility of the drive rack 110A and other internal components from the user as the piston 110 is axially translated within the barrel 58.

The novel variable rate drive mechanisms of the present invention may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. As the end-of-dose indication is tied to the piston reaching the end of its axial translation, the drive mechanism and drug pump provide a true end-of-dose indication to the user. Additionally or alternatively, an electromechanical status switch and interconnect assembly may be utilized to contact, connect, or otherwise enable a transmission to the power and control system to signal end-of-dose to the user. For example, the status switch may be located distal to the pierceable seal 56 and the interconnect located proximal to the plunger seal 60 such that, upon substantially complete axial translation (and the optional compliance push) of the plunger seal 60 within the barrel 58, the status switch and interconnect coordinate to enable a transmission to the power and control system to signal end-of-dose to the user. This configuration further enables true end-of-dose indication to the user.

Figure 7:
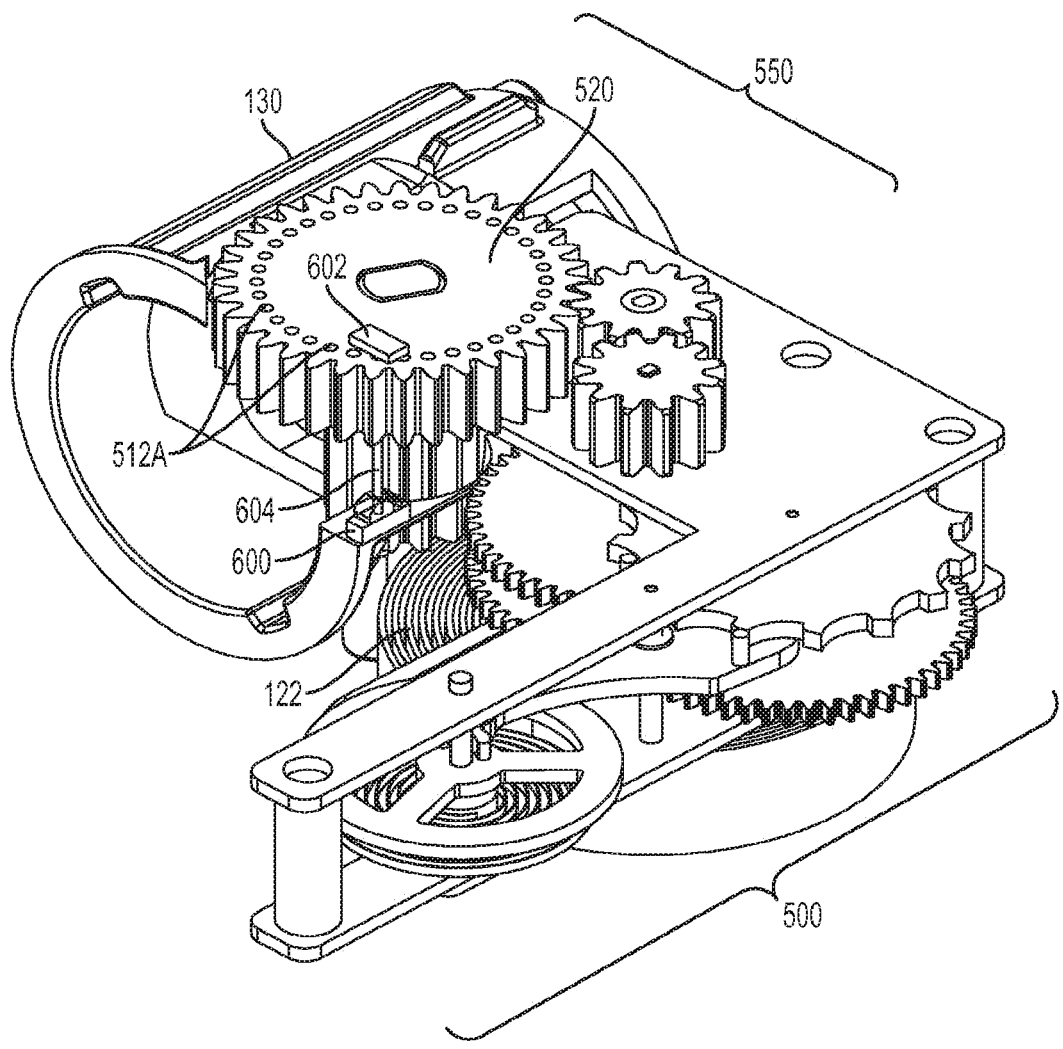
FIG. 7 shows an isometric view of a controlled delivery drive mechanism which incorporates a status indicator, according to at least one embodiment of the present invention.

In at least one embodiment, as shown in FIG. 7, incremental status indication may be provide to the user by reading or recognizing the rotational movement of drive gear 520. As the drive gear 520 rotates, a status reader 600 may read or recognize one or more corresponding status triggers on the drive gear 520 to provide incremental status indication before, during, and after operation of the variable rate controlled delivery drive mechanism. A number of status readers may be utilized within the embodiments of the present invention. For example, the drive mechanism shown in FIG. 7 may utilize a mechanical status reader 600 which is physically contacted by gear teeth of the drive gear 520. As the status reader 600 is contacted by the status trigger(s), which in this exemplary embodiment may be the gear teeth of the drive gear 520 (or holes, pins, ridges, markings, electrical contacts, or the like, upon the drive gear 520), the status reader 600 measures the rotational position of the drive gear 520 and transmits a signal to the power and control system for status indication to the user. Additionally or alternatively, the drive mechanism shown in FIG. 7 may utilize an optical status reader 600. The optical status reader 600 may be, for example, a light beam that is capable of recognizing a motion and transmitting a signal to the power and control system. For example, the drive mechanism may utilize an optical status reader 600 that is configured to recognize motion of the gear teeth of the drive gear 520 (or holes, pins, ridges, markings, electrical contacts, or the like, upon the drive gear 520). Similarly, the status reader 600 may be an electrical switch configured to recognize electrical contacts on drive gear 520. In any of these embodiments, sensor 602 may be utilized to then relay a signal to the power and control system 400 to provide feedback to the user.

As would be appreciated by one having ordinary skill in the art, optical status readers and corresponding triggers, electromechanical status readers and corresponding triggers, and/or mechanical status readers and corresponding triggers may all be utilized by the embodiments of the present invention to provide incremental status indication to the user. While the drive mechanisms of the present invention are described with reference to the gear transmission, gear train, and escapement regulating mechanism shown in FIG. 7, a range of configurations may be utilized for these components with the appropriate gear reduction based on the load and power spring chosen would be acceptable and capable of being employed within the embodiments of the present invention, as would readily be appreciated by an ordinarily skilled artisan. Accordingly, the embodiments of the present invention are not limited to the specific gear transmission, gear train, and escapement regulating mechanism described herein, which is provided as an exemplary embodiment of such mechanisms for employment within the controlled delivery drive mechanisms and drug delivery pumps.

Returning now to the embodiments shown in FIGS. 5A-5C and FIGS. 6A-6C, a fluid, such as a drug fluid, may be contained within barrel 58, in a drug chamber 21, between plunger seal 60 and pierceable seal 56, for delivery to a user. The pierceable seal is adjacent or retained at least partially within cap 52. Upon activation by the user, a fluid pathway connection may be connected to the drug container through the pierceable seal. As described above, this fluid connection may be facilitated by a piercing member of the fluid pathway connection which pierces the pierceable seal and completes the fluid pathway from the drug container, through the fluid pathway connection, the fluid conduit, the insertion mechanism, and the cannula for delivery of the drug fluid to the body of the user. Distal translation of the piston 110 and plunger seal 60, but the drive mechanisms and regulating mechanisms described herein, continues to force fluid flow out from barrel 58 through pierceable seal 56. In at least one embodiment, an end-of-dose status indication may be provided to the user once the status reader recognizes a status trigger positioned on the drive gear to substantially correspond with the end of axial travel of the piston 110 and plunger seal 60. The novel escapement regulating mechanism 500 and drive mechanisms 100 of the present invention thus permit, meter, or otherwise restrain the free axial expansion of the biasing member 122 to control the rate or profile of drug delivery. The novel embodiments of the present invention also thus provide incremental status indication to the user.

Assembly and/or manufacturing of variable rate controlled delivery drive mechanism 100, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 50 may first be assembled and filled with a fluid for delivery to the user. The drug container 50 includes a cap 52, a pierceable seal 56, a barrel 58, and a plunger seal 60. The pierceable seal 56 may be fixedly engaged between the cap 52 and the barrel 58, at a distal end of the barrel 58. The barrel 58 may be filled with a drug fluid through the open proximal end prior to insertion of the plunger seal 60 from the proximal end of the barrel 58. An optional connection mount 54 may be mounted to a distal end of the pierceable seal 56. The connection mount 54 may guide the insertion of the piercing member of the fluid pathway connection into the barrel 58 of the drug container 50. The drug container 50 may then be mounted to a distal end of drive housing 130. The piston 110 having a drive rack 110A may be mounted into the drive mechanism housing 130 and connected to drive pinion 120 and gear drive gear 520. The drive pinion 120 is placed in position adjacent the drive mechanism housing 130 such that it extends at least partly into the drive housing 130 to engage the drive rack 110A for operation.

A fluid pathway connection, and specifically a sterile sleeve of the fluid pathway connection, may be connected to the cap and/or pierceable seal of the drug container. A fluid conduit may be connected to the other end of the fluid pathway connection which itself is connected to the insertion mechanism such that the fluid pathway, when opened, connected, or otherwise enabled travels directly from the drug container, fluid pathway connection, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug pump, as shown in FIG. 1B.

Certain optional standard components or variations of drive mechanism 100, or drug pump 10, are contemplated while remaining within the breadth and scope of the present invention. For example, upper or lower housings may optionally contain one or more transparent or translucent windows 18, as shown in FIG. 1A, to enable the user to view the operation of the drug pump 10 or verify that drug dose has completed. Similarly, the drug pump 10 may contain an adhesive patch 26 and a patch liner 28 on the bottom surface of the housing 12. The adhesive patch 26 may be utilized to adhere the drug pump 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug pump 10 in contact with the body of the user. Removal of the patch liner 28 may further remove the sealing membrane 254 of the insertion mechanism 200, opening the insertion mechanism to the body of the user for drug delivery (as shown in FIG. 1C).

Similarly, one or more of the components of controlled delivery drive mechanism 100 and drug pump 10 may be modified while remaining functionally within the breadth and scope of the present invention. For example, as described above, while the housing of drug pump 10 is shown as two separate components upper housing 12A and lower housing 12B, these components may be a single unified component. As discussed above, a glue, adhesive, or other known materials or methods may be utilized to affix one or more components of the variable rate controlled delivery drive mechanism and/or drug pump to each other. Alternatively, one or more components of the variable rate controlled delivery drive mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the drive mechanisms and drug pumps disclosed herein provide an efficient and easily-operated system for automated drug delivery from a drug container. The novel embodiments described herein provide drive mechanisms for the controlled delivery of drug substances and drug delivery pumps which incorporate such drive mechanisms. The drive mechanisms of the present invention control the rate of drug delivery by metering, providing resistance, or otherwise preventing free axial translation of the plunger seal utilized to force a drug substance out of a drug container and, thus, are capable of delivering drug substances at desired rates and/or delivery profiles. Additionally, the drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. The novel drive mechanisms of the present invention may be directly or indirectly activated by the user. Furthermore, the novel configurations of the controlled delivery drive mechanism and drug pumps of the present invention maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly.

Manufacturing of a drug pump includes the step of attaching both the controlled delivery drive mechanism and drug container, either separately or as a combined component, to an assembly platform or housing of the drug pump. The method of manufacturing further includes attachment of the fluid pathway connection, drug container, and insertion mechanism to the assembly platform or housing. The additional components of the drug pump, as described above, including the power and control system, the activation mechanism, and the control arm may be attached, pre-formed, or pre-assembled to the assembly platform or housing. An adhesive patch and patch liner may be attached to the housing surface of the drug pump that contacts the user during operation of the device.

A method of operating the drug pump includes the steps of: activating, by a user, the activation mechanism; displacing a control arm to actuate an insertion mechanism; and actuating a power and control system to activate a controlled delivery drive mechanism to drive fluid drug flow through the drug pump according to a controlled rate or drug delivery profile. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the controlled delivery drive mechanism by the force applied by a torsional power spring acting upon (directly or indirectly) a piston within a drug container to force fluid drug flow through the drug container, the fluid pathway connection, a sterile fluid conduit, and the insertion mechanism for delivery of the fluid drug to the body of a user, wherein a regulating mechanism acting to restrain the force applied by the power spring is utilized to meter the free axial translation of the piston. The method of operation of the insertion mechanism and the drug pump may be better appreciated with reference to FIGS. 5A-5C and FIGS. 6A-6C, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A controlled delivery drive mechanism comprising:
a drug container having a barrel and a plunger seal;
a drive housing including a linear power spring and a piston having an interface surface and a drive rack, wherein the linear power spring is coupled, directly or indirectly, to the piston and to a gear train, a drive pinion engaging the drive rack of the piston and the gear train diverting at least a portion of a force provided by the linear power spring to power a regulating mechanism capable of engaging the drive pinion to control the rate of rotation of the drive pinion;
wherein the piston is configured to contact and axially translate the plunger seal within the barrel, and wherein the regulating mechanism meters the drive pinion such that the piston is axially translated at a controlled rate by the linear power spring.

2. The drive mechanism of claim 1, wherein the drug container contains a drug fluid within a drug chamber for drug delivery at the controlled rate.

3. The drive mechanism of claim 1, wherein the regulating mechanism is an escapement regulating mechanism.

4. The drive mechanism of claim 3, wherein the escapement regulating mechanism comprises a lever and an escape wheel configured to engage and meter a rotational movement of the gear train.

5. The drive mechanism of claim 4, wherein the lever has pins and a prong, wherein the prong movably engages the post, and is configured to removably engage an impulse pin of a balance wheel, and wherein the balance wheel engages and is capable of oscillating around a post in combination with a hair spring.

6. The drive mechanism of claim 4, wherein the escape wheel is a compound gear having escape teeth around a circumference of a large diameter escape gear and a small diameter gear configured to engage and meter the gear train.

7. The drive mechanism of claim 1, wherein the regulating mechanism is an escapement regulating mechanism, and wherein metering of the drive pinion and by the escapement regulating mechanism controls a rate or profile of drug delivery to a user.

8. A drug delivery pump, comprising:
a housing;
an activation mechanism;
an insertion mechanism;
a fluid pathway connection;
a power and control system; and
a controlled delivery drive mechanism comprising:
  a drug container having a barrel and a plunger seal;
  a drive housing including a linear power spring and a piston having an interface surface and a drive rack, wherein the linear power spring is coupled, directly or indirectly, to the piston and to a gear train, a drive pinion engaging the drive rack of the piston and the gear train diverting at least a portion of a force provided by the linear power spring to power a regulating mechanism capable of engaging the drive pinion to control the rate of rotation of the drive pinion;
  wherein the piston is configured to contact and axially translate the plunger seal within the barrel, and wherein the regulating mechanism meters the drive pinion such that the piston is axially translated by the linear power spring at a controlled rate for drug delivery.

* * * * *